United States Patent [19]

Thurner et al.

[11] 4,308,751

[45] Jan. 5, 1982

[54] METHOD FOR INVESTIGATING AN ANCHORED ROD-LIKE BODY HAVING AN ACCESSIBLE END, AND APPARATUS FOR CARRYING OUT THE METHOD

[76] Inventors: Heinz F. Thurner, Bunsövägen 29, S-132 00 Saltsjö-Boo; Ake J. Sandström, Flisbacken 37, S-191 51 Sollentuna; Christer N. Svensson, Sunnanvägen 9-11, S-146 00 Tullinge, all of Sweden

[21] Appl. No.: 29,005

[22] Filed: Apr. 11, 1979

[30] Foreign Application Priority Data

Apr. 13, 1978 [SE] Sweden .................. 7804161

[51] Int. Cl.³ ............................................. G01N 29/04
[52] U.S. Cl. ........................................ 73/627; 73/628; 73/778
[58] Field of Search ............... 73/627, 628, 630, 632, 73/761, 581, 778; 116/DIG. 4; 310/334, 336

[56] References Cited

U.S. PATENT DOCUMENTS

| | | | |
|---|---|---|---|
| 2,625,035 | 1/1953 | Firestone | 73/632 |
| 3,306,100 | 2/1967 | Wilhelm et al. | 73/581 |
| 3,810,385 | 5/1974 | McFaul et al. | 73/581 |
| 4,062,227 | 12/1977 | Heyman | 73/630 |
| 4,191,904 | 3/1980 | Massa | 310/334 |
| 4,198,865 | 4/1980 | Tarpley et al. | 73/761 |

*Primary Examiner*—Anthony V. Ciarlante
*Attorney, Agent, or Firm*—Jon M. Lewis

[57] ABSTRACT

A method and apparatus for investigating a rod-like body which is anchored in a surrounding material and which has an accessible end, for determining the state of the anchorage of the body and its length. Transient elastic oscillations are excited in the accessible end of the body. The oscillations comprise a flexural wave causing a deformation of the body varying with respect to amplitude and phase over the cross-section of the body. The flexural wave propagates in the longitudinal direction of the body and is partially reflected at discontinuities of the body and/or the anchorage. Transient elastic ocillations comprising flexural waves reflected at such discontinuities and returning to the accessible end of the body are received and detected. The position and magnitude and/or type of at least some of the discontinuities are estimated with the aid of time-position and amplitude of the reflected flexural waves. Discontinuities of interest are the beginning and end of anchorage, the end of the body and possible cracks or fractures in the body and/or its anchorage.

The method and the apparatus are primarily intended for in-situ investigation of concrete-bond rock anchors (bolts), although the method and apparatus can be used for at least partially investigating other anchored rod-like bodies.

18 Claims, 20 Drawing Figures

METHOD FOR INVESTIGATING AN ANCHORED ROD-LIKE BODY HAVING AN ACCESSIBLE END, AND APPARATUS FOR CARRYING OUT THE METHOD

FIELD OF INVENTION

The present invention relates to a method of investigating an anchored rod-like body having an accessible end, and apparatus for carrying out the method. The method and apparatus are primarily intended for investigating the state of anchorage of the body and the length of the body and for determining the presence or absence of any substantial discontinuities therein or therealong, although the method and apparatus are not limited to such use, but can also be used for other investigations.

The method and apparatus are primarily intended for investigating concrete-bond bolts, although said method and apparatus are not limited heretofor but can be used, either completely or partially for investigating other anchored rod-like bodies, such as ground anchor rods, concrete-reinforcing rods and embedded pipe lines etc. By "concrete-bond" is meant that the bolt is anchored, e.g. in the wall or roof of a rock tunnel, by a concrete bond, either at one end or at one or more positions between the ends.

By state of the anchorage of the body is meant here the length of the bond or anchorage by which the body is fixed in the surrounding material and its localization along said body, and the extent of the contact of the body with said surrounding material. The state of the anchorage of the body, the length of the body and any other discontinuities therein all have an effect on the ability of the rod to take up or transmit loads.

By an accessible end of an anchored rod-like body is meant either a free end projecting a distance out of the anchorage or an end having at least the end surface free from the anchorage and accessible for direct mechanical contact with means for generating and detecting transient elastic oscillations in the body.

BACKGROUND OF THE INVENTION

Conventional methods of mounting bolts, for example to strengthen the roof and walls of rock tunnels, do not in themselves offer a guarantee that the bolts are satisfactorily anchored in the rock. It is not possible to visually determine whether, for example, a concrete-bonded bolt has the prescribed length or that the bond is satisfactory, i.e. it has the desired load-carrying or load-transmitting abilities. Further it is possible for a bolt which was originally mounted correctly and which initially was in good contact with the surrounding rock and was sufficiently load-carrying, to subsequently become loose and at least loose a considerable part of its load-carrying ability. This may occur, for example, as a result of the bolt being subjected to shear forces or tension forces as a result of movement in the surrounding rock. If the bolt should fracture, it is impossible to detect the fracture visually, even though the fracture should occur at only a very short distance from the outer surface of the concrete-bond. There is thus a need for methods and means of checking the length and the function of bolts.

One method of checking the anchorage of a bolt and its load-carrying ability is to apply a tension force to the bolt, by means of a hydraulic jack for example, until the bolt fractures or loosens. Because of the costs involved and the amount of time required, normally only a small percentage of the total number of bolts can be checked. Furthermore, the load-carrying ability of the bolts and the corrosion-protective effect of the concrete bond can be impaired by subjecting them to tensile tests, rendering the tested bolt unserviceable, even though the bolt has not been pulled until it loosens or fractures. Furthermore, such tensile tests have a limited value, since it has been established that a bonding length of about 30 cm is sufficient to hold the bolt such as to cause the bolt to fracture when a tensile load is applied thereto. Thus, a tensile test in which the end of the bolt fractures only shows that the bolt had a satisfactory bond length of at least approximately 30 cm.

The object of the present invention is to provide means in which the length of rod-like elements, such as rock bolts and the like, and the anchorage conditions thereof can be nondestructively investigated in-situ without causing damage to said elements or impairing said anchorage. Thus, a rock bolt or like element subsequent to being tested shall be capable of being used for reinforcing purposes or for load-carrying purposes or for other purposes. By subjecting all, or a sufficient number of selected bolts within a given limited area to such a non-destructive examination, it is possible to establish whether the reinforcement of a wall or a roof structure is sufficient, with respect to prescribed safety requirements. The non-destructive examination is made with the help of elastic oscillations.

It has long been known that elastic oscillations of a multiplicity of different wave types, can, under certain conditions, propagate along a circular-cylindrical homogenous body. Examples of such wave types include longitudinal waves, torsional waves, radial waves and flexural waves. When the oscillations have a sufficiently high frequency it is generally possible for more than one oscillation mode of respective wave types to propagate along the circular-cylindrical body. If, for the sake of simplicity, one limits oneself to the simplest oscillation mode of respective wave type and the lowest frequency thereof, it is relatively simple to describe the different wave types in a manner such that their differences are clearly apparent. The oscillation mode of the longitudinal wave is characterized by the fact that the entire cross section of the body is alternately compressed and expanded in the longitudinal direction thereof. The oscillation mode of the radial wave is characterized by the fact that the entire cross section of the body is alternately compressed and expanded in the radial direction. The oscillation mode of the torsion wave is characterized by the fact that adjacent cross sections of the body twist relative to each other around the axis of the body. The oscillation mode of the flexural wave is characterized by the fact that certain parts of a cross-section of the body expand in the longitudinal direction thereof at the same time as other parts of said cross-section are compressed in the said longitudial direction. The said parts are separated by a diametrical, neutral plane located parallel with the sense of propagation of the oscillation mode, i.e. with the longitudinal axis of the circular-cylindrical body.

For a more exhaustive description of elastic waves in rod-like bodies, reference is made to the article "Elastic Waves in Rods and Clad Rods", by R. N. Thurston, published in the Journal of Acoustical Society of America, 64 (1), July 1978.

The propagation of waves through a concrete-bonded bolt is, for a number of reasons, more complicated to describe theoretically than the wave propagation in a circular-cylindrical homogenous free body. One reason, of course, is because the bolt is bonded in concrete and consequently not free. The contact of the concrete bond with the outer surfaces of the bolt causes certain restrictions to the possible compression and expansion of the cross-section of the bolt, at least in those parts of said cross-section lying closest to the said outer surface of the bolt. Another reason is that bolts do not normally have the form of a circular-cylindrical body. The majority of bolts today comprise reinforcing rods provided with a multiplicity of shoulders or teeth along their outer surfaces.

The shoulders extend either tangentially at right angles to the longitudinal axis of the bolt, or at an oblique angle to said axis. Neither do the shoulders extend completely around the circumference of the bolt, but that certain bolts have peripheral portions which are not provided with such shoulders. In certain cases, the peripheral surface of the bolts may also be provided with one or two shoulders which extend in the longitudinal direction of the bolt. The result is that the cross-sectional shape of the bolt is neither circular nor constant therealong, but varies substantially along the length of said bolt.

For a more exhaustive description of wave propagation in rod-like elements which may vary in cross-section along the length thereof, reference is made to the article "Wave Propagation in Non-uniform Elastic Rods" by Gerald Rosenfeld and Joseph B. Keller, published in the Journal of the Acoustical Society of America, volume 57, number 5, May 1975, pages 1094–1096.

SUMMARY OF THE INVENTION

The invention is based upon the concept of exciting transient elastic oscillations in the free end of a rod-like element which is anchored at one end thereof in a surrounding material. Such an oscillation propagates along the body and its anchorage at a speed and with a degree of damping which are dependent upon certain wave-propagation parameters. At discontinuities in the bolt and/or its anchorage and/or the material surrounding the bolt there occur reflected oscillations of a magnitude, type and direction which are dependent upon the geometric conditions and wave-propagation parameters, which are at least partially connected with the physical parameters of the bolt, the anchorage and the surroundings. By detecting such reflected transient elastic oscillations and interpreting and analyzing the parameters of said oscillations, such as time of arrival, frequency, amplitude, mode etc., it is possible in accordance with the invention to obtain certain information about at least certain discontinuities.

Discontinuities which are of interest in respect of the ability of a concrete-bonded bolt to carry or transmit loads are primarily those located at the beginning and at the end of the bolt, the state of the concrete bond of the bolt, and possible cracks or fractures in the bolt and its anchorage. The contact of the concrete bond with the bolt and surrounding rock is also significant to the load-carrying or load-transmitting ability of the bolt. This contact influences the damping of the transient elastic oscillation and to a certain extent also its speed of propagation. By relating the amplitude of reflected oscillations to arrival-time and the amplitude of generated oscillations, it is thus possible to obtain indirectly some information concerning said contact.

The use of oscillations or vibratory movements for the non-destructive testing or checking of elements is, of course, not new per se. Material testing with the aid of ultrasonics and like methods has long been known. Testing in accordance with the present invention, however, differs from conventional ultrasonic testing, both with respect to excitation and detection and to the analysis of the oscillations.

The present invention is based on the concept of exciting and detecting transient transverse flexural waves, even in combination with longitudinal waves and/or torsion waves. It has been surprisingly found that the simplest, lowest-frequency oscillation mode of flexural waves is dampened to a much smaller extent when propagating in a concrete-bonded bolt made from reinforcing rod than, for example, the simplest, lowest-frequency oscillation mode of longitudinal waves of comparable frequency.

Although, in accordance with the invention, it is mainly flexural waves which are excited, it is not possible, as a result of the anchorage of the bolt and the varying cross-sectional shape of said bolt, to exclude the fact that elastic oscillations of other wave types and/or oscillation modes are excited along the concrete-bonded bolt, at least at sufficiently high oscillation frequencies. Neither is it possible to fully exclude the fact that such elastic oscillations are coupled, in some way or another, to the original excited oscillation and propagated in conjunction therewith when the oscillation is of a certain frequency. It is possible, however, to completely or partially separate reflected oscillations of different wave types one from the other by suitable design of the means by which the reflected elastic oscillations are received. For a more exhaustive description of such excitation along a rod and said coupling, reference is made to the article "Experimental Study on the Wave Mode in Elastic Cylindrical Rod" by Toda Fukuoka Tanida, published in the bulletin of Japan Society of Mechanical Engineers, volume 19, number 132, June 1976, pages 590–594.

So that the invention will be more readily understood and further features thereof made apparent, exemplary embodiments of the method and apparatus according to the invention will now be described with reference to the accompanying drawings.

DETAILED DESCRIPTION OF PREFERRED EMBODIMENTS

Figure 1:
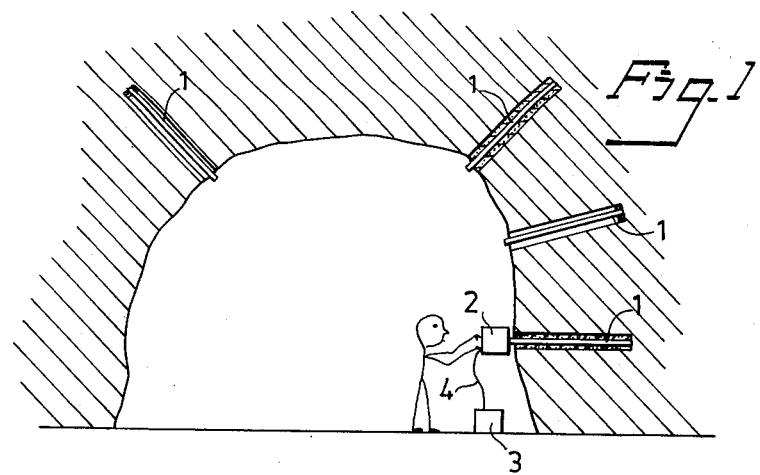
FIG. 1 illustrates the investigation of a rock bolt fixed in the wall of a rock tunnel.

In FIG. 1 there is illustrated a tunnel which has been formed in rock for example. Mounted in the roof and walls of the tunnel is a plurality of so-called rock bolts 1, each of said bolts having an end which projects freely into the tunnel. Some of the bolts my be free bolts, i.e. bolts that are anchored only at the bottom of the bore hole while others are anchored in the rock by means of concrete bonds. When investigating a concrete-bonded bolt, a hand tool 2 is pressed against the free end of the bolt, said free end having been made flat or smooth prior to the investigation. The hand tool comprises one part of a two-part device for investigating the status of the bolt and comprises means for exciting and detecting given transient elastic oscillations in the outwardly projecting free end of the bolt. The hand tool and the said second part 3 of the device are connected together by means of an electric cable 4.

The transient elastic oscillations excited in the free end of the bolt propagate in the longitudinal direction thereof and give rise to reflected elastic transient oscillations at the beginning of the concrete bond and at other discontinuities, such as the end of the concrete bond and the end of the bolt, and at possible fractures in the bolt. During their propagation along the bolt in the axial direction thereof, from and towards the free end of said bolt, the elastic oscillations are dampened to an extent which depends, inter alia, on the extent to which the concrete bond is in contact with the bolt and with the surrounding rock.

The wave propagation velocities and the damping of transient elastic waves can be determined by measuring free bolts and bonded bolts of known lengths and known cross-sectional dimensions and anchoring conditions. The amplitude and shape of reflected oscillations which occur with different types and sizes of discontinuities of such anchorages and bolts can also be determined by measuring a multiplicity of discontinuities of known type and size. The hand tool and the said second part of the testing device together contain means which set the time position and/or amplitude and, optionally, other parameters of the received transient elastic oscillations in relations to pre-determined wave propagation velocities and damping etc., and give certain information about those discontinuities of the bolts and their anchorages at which the received reflected oscillations have occurred. The information may be of a more or less sophisticated nature and may be presented by presentation means on the hand tool or the said second part of the device, or may be stored on magnetic tapes or the like. The invention relates specifically to the selection of excited and received wave types and oscillation modes, the means for exciting and receiving these wave types, and the manner in which the signals are processed in the present context.

Figure 2:
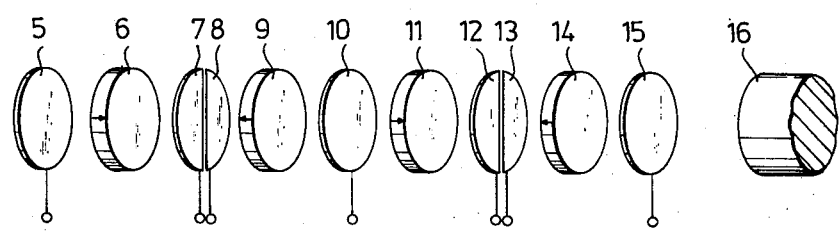
FIG. 2 is an exploded view of means for exciting and detecting elastic flexural waves and longitudinal waves in a free end of a fixed, rod-like body.

The purpose of FIG. 1 is merely to illustrate the field of use and the use of the invention. In fact a complete hand tool 2 can be modified and improved. The mechanical construction and design of the hand tool is believed to be of subordinate importance except for the device which excites and receives the transient elastic oscillations and the suspension of said device in the hand tool. Generally the suspension should be such as to suppress the generation of reflected waves in the hand tool. This is believed to be achieved by at least partially embedding said device in rubber and/or other soft material such as soft foamed synthetic resins. FIG. 2 is an exploded view of parts of an embodiment of said means for exciting and receiving compression waves and flexural waves.

As will be seen from FIG. 2, said means comprises for example four piezo-electric (lead-zirconium-titanate) crystals 6, 9, 11 and 14 each of which is a one piece, cylindrical structure with planar mutually parallel end surfaces. The crystals each have an outer diameter of 25 mm and a thickness of 2 mm. The piezo-electric crystals are polarized at right angles to the parallel end surfaces thereof, i.e. parallel with their respective symmetry axes.

The first two piezoelectric crystals 6 and 9 are arranged between two brass electrodes 5 and 10 of circular cross-section and having a thickness of 0.05 mm, in a manner such that the directions of polarization of the two crystals are opposite to one another. Arranged between the two crystals 6 and 9 are two semi-circular, thin metal electrodes 7 and 8. The two electrodes 7 and 8 are spaced apart such as to leave a narrow, electrically insulating gap therebetween.

In a similar manner to the crystals 6 and 9, the crystals 11 and 14 are arranged between two circular, thin metal electrodes 10 and 15. Two semi-circular electrodes 12 and 13 are arranged between the crystals 11 and 14 in a manner similar to the semi-circular electrodes 7 and 8.

The various crystal-parts and the electrodes are bonded together by means of a two-component epoxy-resin adhesive.

When exciting and receiving transient elastic oscillations, the means shown in FIG. 2 is held, in the bonded state, in the hand tool with the electrode 15 urged against the accessible end of the bolt 16. This end of the bolt has previously been made flat and smooth, by cutting and grinding or in some other manner. The contact surface between the electrode and said end surface is conveniently provided with a small quantity of contact-medium, such as vaseline.

Excitation of oscillations is effected by commonly connecting the three whole electrodes 5, 10 and 15 to earth potential and by applying an electric voltage to the semi-circular electrodes 7 and 8. When alternating-voltage pulses of mutually the same amplitude and phase are applied to the semi-circular electrodes 7 and 8, the crystals 6 and 9 will attempt to move the whole electrodes 5 and 10 alternately towards and away from each other in a planar-parallel fashion, and in this way give rise to a longitudinal oscillation. If, on the other hand, alternating-voltage pulses of mutually the same amplitude but a phase difference of 180° are applied to the two semi-circular electrodes 7 and 8, the crystals 6 and 9 will attempt simultaneously to move the one halves of the electrodes 5 and 10 towards each other and the other halves of the electrodes 5 and 10 away from each other, and vice versa, and in this way give rise to a flexural mode of wave movement.

Detection of the oscillations is effected with the crystals 11 and 14 and the semi-circular electrodes 12 and 13. Because the detecting electrodes 12 and 13 and the excitation electrodes 7 and 8 are electrically separated by the electrically insulating crystal material, the receiving of waves and the excitation of waves can be carried out simultaneously.

Detection of the oscillations is effected by commonly connecting the three whole electrodes 5, 10 and 15 to earth potential. If the two piezo-electrical crystals 11 and 14 are subjected to a deforming force by a received oscillation, an electric charge is obtained on the electrodes 12 and 13. If, for the sake of simplicity, it is assumed that the capacitance between the electrodes and earth and the modulus of elasticity of the crystals is constant, there is obtained a voltage on the electrodes which is substantially proportional to the deformation.

Figure 3:
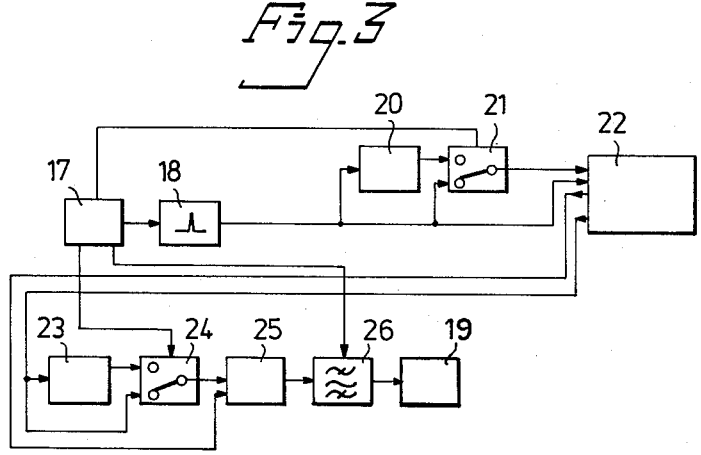
FIG. 3 is a block schematic of an apparatus for investigating a fixed, rod-like body.

FIG. 3 is a block schematic illustrating a device for testing a rod-like body which is fastened or anchored in a surrounding material, by exciting and detecting transient elastic waves by the device shown in FIG. 2. For reasons of simplicity the whole device of FIG. 2 is represented by a block given reference number 22 in FIG. 3. The two inputs of block 22 represent the electric leads to semi-circular electrodes 7 and 8 respectively. The two outputs of block 22 represent the electric leads to semi-circular electrodes 12 and 13 respectively. Since electrodes 5, 10 and 15 are grounded during excitation and detection these are not shown in FIG. 3. In the FIG. 3 embodiment a signal generator 18 generates, in dependence upon a control means 17, a pulse with comprises one or a few sinusoidal periods of suitable frequency. In the case of concrete-bonded bolts made from reinforcement bars and having a diameter of about 25 mm, the frequency should be between 20 and 100 kHz. The output of the signal generator is connected to an inverter 20, a switching device 21 and an input of the excitation and detection device 22. The switching device 21 has two inputs, of which the second is connected to the output of the inverter 20. The output of the switching device 21 is connected to the other input of the excitation and detection device. The upper and lower inputs of the excitation and detection device 22 are connected to semi-circular electrodes 7 and 8 respectively. When the switching device 21 is coupled in the specific manner, indicated in FIG. 3, alternating-voltage pulses of mutually the same amplitude and phase are applied to the inputs of the excitation and detection device 22, said pulses generating longitudinal oscillatory movements. When the switching device 21 is coupled in the other specific manner, alternating-voltage pulses of mutually the same amplitude but with a phase difference of 180° are applied to the inputs of the excitation and detection device, said pulses giving rise to oscillations of the flexural mode.

The electric leads of the electrodes 12 and 13 in the excitation and detection device 22 are coupled to a signal-processing line comprising an inverter 23, a bistable switching device 24, a summation device 25, a band-pass-filter 26 and an oscilloscope 19.

The voltage from the electrode 12 is applied to a summation device 25. The voltage from the electrode 13 is applied to an inverter 23 and to one input of the two-stage switch 24. The output of the switch 24 is connected to the other input of the summation device 25.

With the switch 24 in the position indicated in FIG. 3, the output signal of the summation device will be proportional to the sum of the two voltages from the electrodes 12 and 13. When the switch 24 is in its other position, there is obtained instead an output signal which is proportional to the difference between the two voltages from the electrodes 12 and 13. By summing the voltages, the detection obtains maximum sensitivity for the lowest oscillation mode of longitudinal waves, while the influence of flexural waves is suppressed. If the difference voltage is formed instead, detection will have its maximum sensitivity for the lowest oscillation mode of flexural waves, while the influence of longitudinal waves will be suppressed.

The switches 21 and 24 can be set synchronously with one another by the control unit 17, such that excitation and detection is effected either in respect of longitudinal oscillating modes or oscillations of the flexural wave mode.

At the same time the pass band of the band-pass-filter 26 may be re-set so that there is used a frequency range which is optimal for each wave mode.

Figure 5:
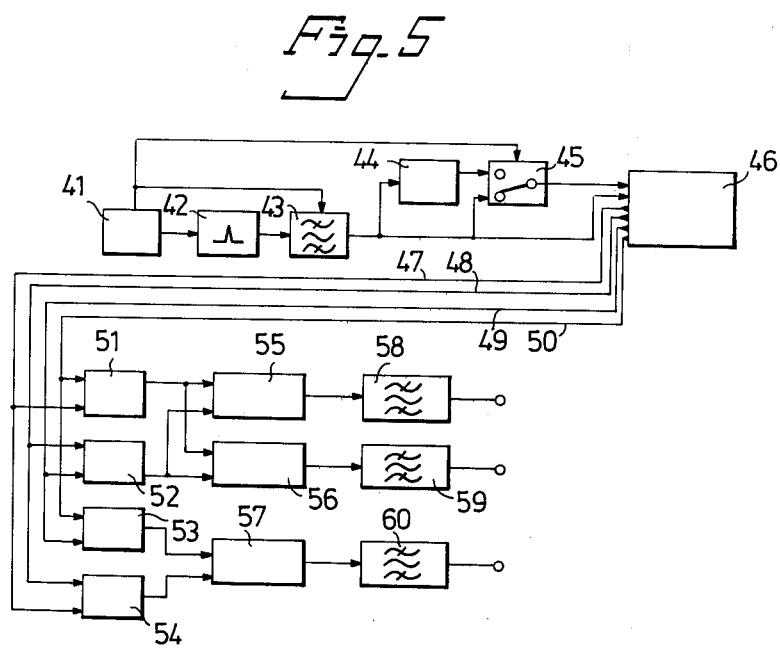
FIG. 5 is a block schematic of an apparatus for investigating a fixed rod-like body with the aid of excitation and detection means according to FIG. 4.

In order to meet the best mode and enabling requirements FIGS. 17-20 show circuit diagrams of embodiments of some of the blocks of FIG. 3 and FIG. 5 although it is believed that one skilled in the art could easily manufacture all of the blocks of FIG. 3 and FIG. 5 from commonly available standard components.

Figure 17:
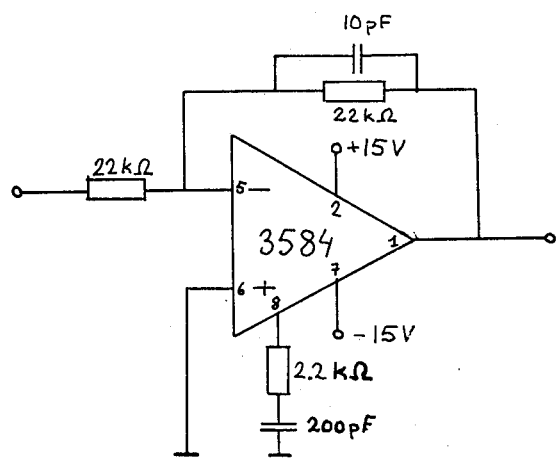
FIGS. 17–20 show circuit diagrams of embodiments of some of the blocks of FIG. 3 and FIG. 5.

FIG. 17 shows a circuit diagram of the inverter 20 in FIG. 3. The inverter is built with an operational amplifier of type Burr Brown 3584 and external components as shown in FIG. 17.

Figure 18:
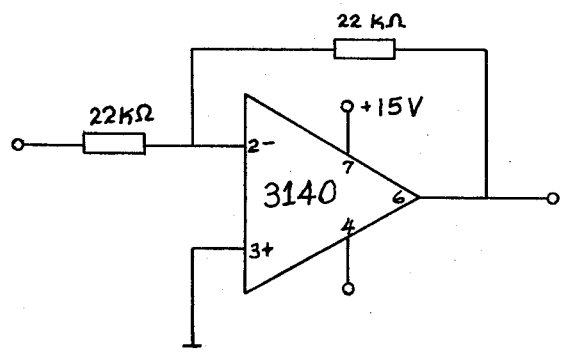

FIG. 18 shows a circuit diagram of inverter 23 in FIG. 3. The inverter is built with an operational amplifier of type RCA 3140 and external components as shown in FIG. 18.

Figure 19:
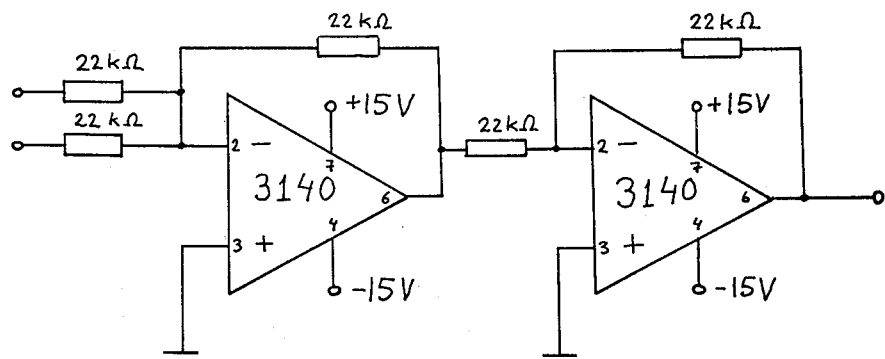

FIG. 19 shows a circuit diagram of the summation device 25 in FIG. 3. The summation device is built with two operational amplifiers RCA 3140 and external components as shown in FIG. 19.

Figure 20:
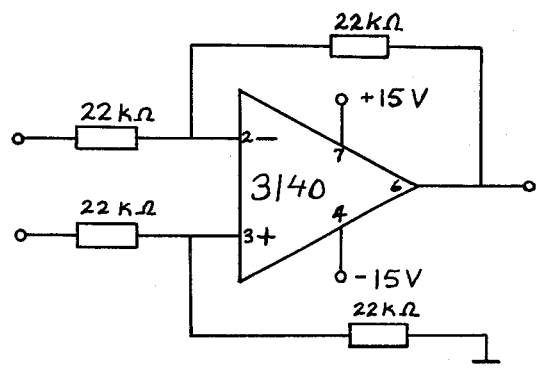

FIG. 20 shows a circuit diagram of a subtractor as used in FIG. 5. The subtractor is built with an operational amplifier of type RCA 3140 and external components as shown in FIG. 20.

The control means 17 consists of a switch to control the switching devices 21 and 24 and a button to trigger the signal generator 18.

The signal generator 18 is a KROHN-HITE Corporation FUNCTION GENERATOR 5300 A used in trig tone burst mode. The band-pass-filter 26 is a KROHN-HITE Corporation VARIABLE FILTER 3202 in band pass mode.

The flexural wave excited in a rod-like body is characterized by a movement around a neutral plane oriented parallel with the propagation axis of the wave, i.e. the longitudinal axis of the bolt. At the moment of excitation, the neutral plane coincides with the gap between the two electrode halves 7 and 8, to which the excitation voltage is applied.

The fact that the orientation of the neutral plane may have changed subsequent to the flexural wave having travelled along the rod, being reflected at the end surface thereof or at other discontinuities, and returning to the outer, free end of the bolt against which the excitation and measuring device is placed cannot be excluded. This change in direction of the said plane may be due to inhomogenities in the bolt, deformations in the bolt or at the bolt surfaces, and to the conditions prevailing at the reflective surface or the end of the bolt (the inner end thereof).

Figure 4:
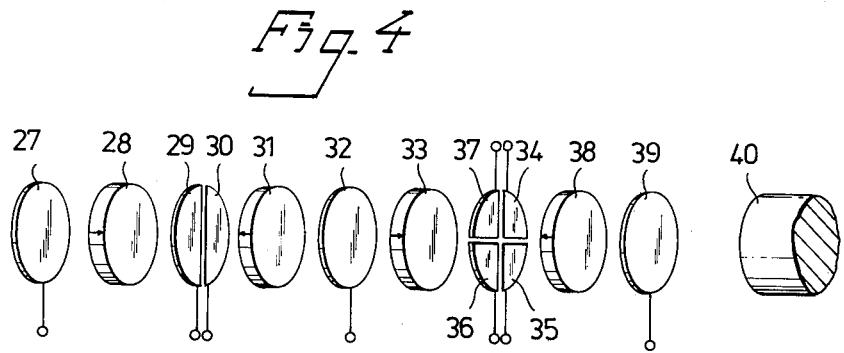
FIG. 4 is an exploded view of means for exciting and detecting elastic flexural waves and longitudinal waves, with the possibility of detecting flexural waves in two orthogonal directions in a free end of a fixed rod-like body.

In order to be able to detect reflected flexural waves in an optimum fashion, the axis of symmetry of the detecting electrodes should coincide with the neutral plane of the flexural wave. One method of achieving this is to design the excitation and detection device in a manner such that the detecting part thereof can be rotated relative to the excitation parts thereof. A more sophisticated solution is one in which the excitation and detection device is constructed in a manner such that it is able to detect flexural waves in any selected axis or in two axes which are at right angles to one another. FIG. 4 illustrates an embodiment of an excitation and detection device which can achieve this.

The embodiment of FIG. 4 is similar to the embodiment of the device shown in FIG. 2, but with the essential difference that the measuring electrodes 12 and 13 are divided into four sectors 34, 35, 36 and 37, as shown, instead of two.

By means of the embodiment of four sectors 34, 35, 36 and 37 of the detection-electrodes of the excitation and detection device shown in FIG. 4, and complementary signal-processing means as shown in FIG. 5, it is possible to detect flexural waves in two orthogonal directions.

The illustrated device comprises four piezo-electric crystals 28, 31, 33 and 38 each of which is a one-piece cylindrical structure with planar-parallel end surfaces. The piezoelectric crystals are polarized at right angles to the said parallel end surfaces, i.e. parallel with the axis of symmetry.

The first two piezoelectric crystals 28 and 31 are arranged between two circular, thin metal electrodes 27 and 32 in a manner such that the directions of polarization of the piezoelectric crystals are mutually oppositely directed. Arranged between the two piezoelectric crystals 28 and 31 are two semi-circular, thin, metal electrodes 29 and 30 in a manner such that they do not meet at their diameters, but are separated by a narrow, electrically insulating gap.

The crystals 33 and 38 intended for detecting the wave are also arranged between two electrodes 32 and 39, in a manner such that the polarization directions of the crystals are opposite to one another.

Arranged between the two detection crystals are four sector-shaped metal electrodes 34, 35, 36 and 37, in a manner such as to be electrically insulated from one another.

FIG. 5 is a block schematic of an apparatus for testing an anchored rod-like body by exciting and detecting transient elastic oscillations by means of the device shown in FIG. 4. For reasons of simplicity the whole device of FIG. 4 is represented by a block given reference number 46. The block has two inputs representing the electric leads to semi-circular electrodes 29 and 30. The block 46 has four outputs representing the leads to sector-shaped electrodes 34, 35, 36 and 37. Since electrodes 27, 32 and 39 are grounded during exciting and detection of oscillations the electric leads to those electrodes are not indicated in FIG. 5.

In FIG. 5 a pulse generator 42 is arranged to generate one or more pulses of short duration in response to a control unit 41, the energy of which pulses is found substantially within the frequency range suitable for the elastic oscillation. The output of the pulse generator is coupled to the input of a band-pass-filter 43. The pulses filtered by the filter are applied to an inverter 44, a switching device 45 and one of the inputs of the excitation and detection device 46. The other input of the switching device 45 is connected to the output of the inverter. The output of the switching device 45 is connected to the other input of the excitation and detection device. The upper and lower inputs of the excitation and detection device 46 are connected to semi-circular electrodes 29 and 30, respectively.

When the switching device 45 is set to the specific setting indicated in FIG. 5, alternating voltage pulses of mutually the same amplitude and phase are applied to the excitation electrodes 29 and 30 of the excitation device 46, whereby longitudinal oscillations are generated. When the switching device 45 is set to the other specific setting, alternating current pulses of mutually the same amplitude but with 180° phase difference are applied to the excitation electrodes 29 and 30 of the excitation device 46, thereby giving rise to oscillations of the flexural wave mode.

The output lines 47, 48, 49 and 50 from the excitation and detection device 46 are each connected to a respective sector-shaped electrode 34, 35, 36 and 37, as shown in FIG. 4.

In the following description it is assumed that the excitation and detection device is oriented in a manner such that its axis of symmetry is horizontal and the upper, right electrode 34 is connected to a line 47. The lower right electrode 35 is connected to a line 48. The lower left electrode 36 is connected to a line 49. The upper left electrode 37 is connected to a line 50.

A summation device 51 is connected to the lines 47 and 50 and in this way produces a signal which is proportional to the sum of the voltages obtained from the two upper electrodes. A summation device 52 is connected to the lines 48 and 49 and in this way produces a signal which is proportional to the sum of the voltages from the two lower electrodes. A summation device 53 is connected to the lines 49 and 50 and in this way produces a signal which is proportional to the sum of the voltages obtained from the two left-hand electrodes. A summation device 54 is connected to the lines 47 and 48 and in this way produces a signal which is proportional to the sum of the voltages obtained from the two right-hand electrodes.

The output signals from the summation device 51 are applied to a further summation device 56 and to a subtractor 55. The output signals from the summation device 52 are also applied to a further summation device 56 and to a subtractor 55, whilst the output signals from the summation devices 53 and 54 are applied to a subtractor 57.

The output signals from the summation device 56 are the sum of the signals obtained from the four detecting electrodes and, in this way, are most sensitive to the longitudinal compression wave, whilst the influence of the flexural wave is suppressed.

The output signals from the subtractor 55 represents the difference between the summation signal from the two upper electrodes and the summation signal from the two lower electrodes. A maximum output signal is obtained for flexural waves having a horizontal neutral plane while flexural waves having a vertical neutral plane and longitudinal compression waves are suppressed.

The output signal from the subtractor 57 represents the difference between the signals obtained from the two right-hand electrodes and the signals from the two left-hand electrodes. A maximum output signal is obtained for flexural waves having a vertical neutral plane, while flexural waves having a horizontal neutral plane and longitudinal waves are suppressed.

The output signal obtained from the subtractor 55 is applied to a band-pass-filter 58. The signal from the other subtractor 57 is applied to a band-pass-filter 60. The output signal from the summation circuit 56 is applied to the band-pass-filter 59.

The possibility that further information concerning at least one further bonded part of a bolt could be obtained by also generating torsional waves and shear waves cannot be excluded. Simple tests in practice have shown, however, that difficulties exist in obtaining a satisfactory mechanical coupling between one flat end of a bolt and the means for generating and detecting torsional oscillations. Possibly satisfactory coupling could be obtained if the accessible end surface of the bolt had the form of two semi-elliptical planar surfaces at angles to each other and to the longitudinal direction of the bolt, instead of flat end-surfaces.

Figure 6:
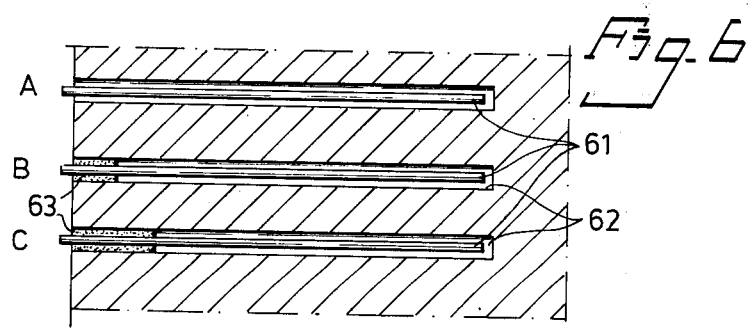
FIG. 6 illustrates a multiplicity of bolts having bonds of different lengths.

FIG. 6 illustrates in cross section three bolts 61 made from reinforcement bar, of which two are shown to be concrete-bonded in bores 62 in granite, the concrete bond 63 of the bolt C being longer than the bond of the bolt B.

The bolt A has not been concrete-bonded and is taken as a reference. Means for suspending bolt A without causing substantial reflections are not shown in FIG. 6 for reasons of simplicity. The bolt B has a concrete bond of about 20 cm of length, while the bond of the bolt C is about 40 cm of length. All the bolts are made from reinforcement bars having a diameter of 25 mm. Each of the bolts has a length of 2250 mm.

The outer ends of the bolts have been cut at right angles to the axes of the bolts, and worked to a surface fineness such that good contact is obtained between the bolt and the excitation and detection means when said means is held pressed against the end of the bolt via a contact medium, which in this case is a grease. The inner ends of the bolts have been cut with bolt shears and have not been especially prepared.

FIGS. 7–15 illustrate signals obtained when investigating the bolts shown in FIG. 6 with the excitation and detection device described with reference to FIG. 2. The device of FIG. 2 was held without casing in the hand of an examiner and was urged by him against the flat end of each bolt respectively so that substantially the whole surface of electrode 15 was in good mechanical contact with the end surface of respective bolt and the centers of electrode surface and flat bolt end surface substantially were coinciding. The remainder of the device was functionally equivalent with the embodiment illustrated in the block schematic of FIG. 3.

Figure 7:
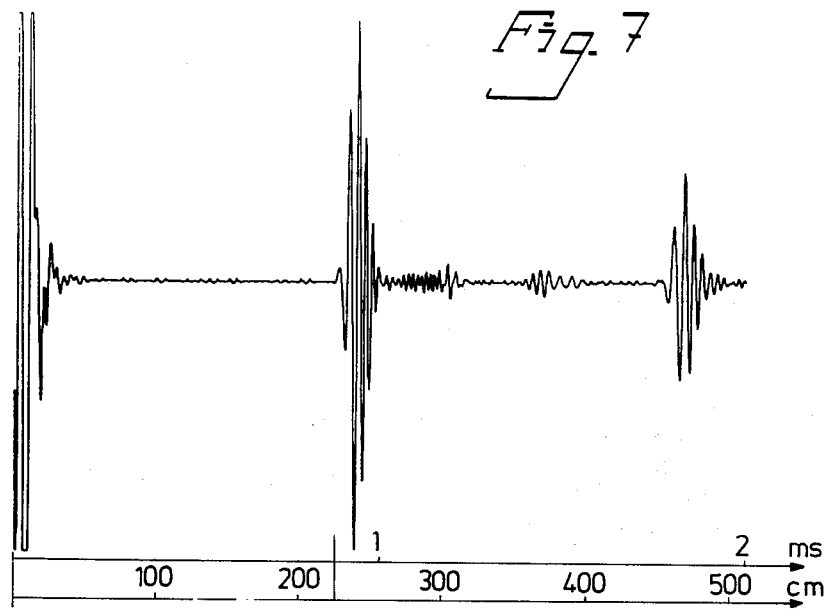
FIGS. 7–15 show the configuration of the signals obtained when investigating rock bolts having bonds of mutually different lengths as shown in FIG. 6.
Figure 8:
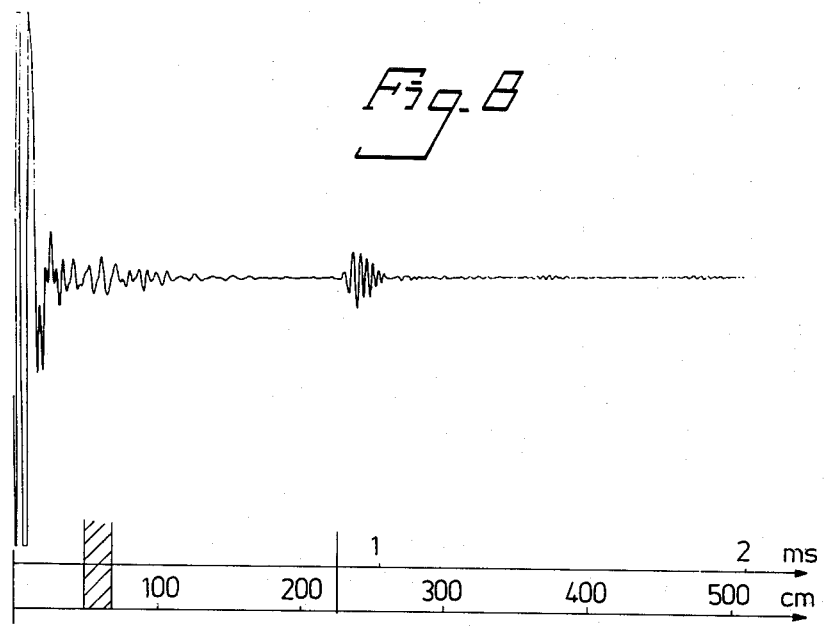
Figure 9:
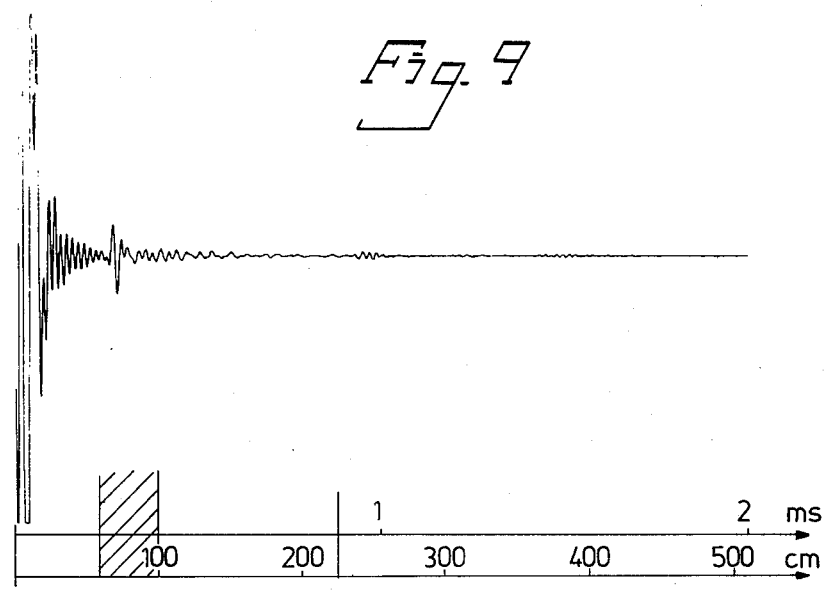

The shape and form of the signals shown in FIGS. 7–9 were obtained on an oscilloscope 19 connected to the output of the bandpass filter 26 with the switching device 21 in a position such that both excitation electrodes 7 and 8 had applied thereto an alternating voltage pulse of mutually the same amplitude and phase. In a corresponding manner, the switching device 24 was set so that the sum of the signals from the two detecting electrodes 12 and 13 was applied to the filter 26. These settings give optimum excitation and detection for the longitudinal wave mode. The filter setting in question provided a passband having a lower limit frequency of 20 kHz and an upper limit frequency of 60 kHz. Excitation was effected with an alternating voltage pulse comprising one period of frequency 40 kHz and an amplitude of 20 volts.

FIG. 7 illustrates the signal when investigating the non-bonded bolt A shown in FIG. 6. It will be seen from the signal configuration that the amplitude of the signal which has been obtained in conjunction with the excitation pulse has been limited in the summation device 25. Subsequent to the decay of the excitation pulse, the signal has a very small amplitude, up to the moment when an oscillation reflected at the other end of the bolt is detected, and can be seen approximately centrally in FIG. 7. The figure also illustrates a number of other detected oscillations which have been reflected more than once against the inner end of the bolt and therefore occur at a later point of time and more to the right in FIG. 7.

With knowledge of the propagation velocity of the longitudinal compression wave, the time-axis of the signal can be converted to a distance axis graduated in centimeters. FIG. 7 illustrates a signal over 2 ms, which has been detected on a loose bolt (the bolt A shown in FIG. 6) having a length of 225 cm. The propagation velocity of the compression wave in respect of the loose bolt has been experimentally determined to be about 5.1 km/s within the frequency band in question. As will be seen from FIG. 7, the actual length of 225 cm of the bolt coincides quite well with the length calculated from the signal, which length is obtained on the distance axis of the Figure during the registration of the reflected oscillation from the inner end of the bolt, shown in the centre of the figure. At the same time the low signal-amplitude from the termination of the excitation pulse to the aforementioned reflection from the bolt end indicates that no essential discontinuities are present along the bolt.

FIG. 8 illustrates the signal obtained when investigating the bolt B shown in FIG. 6, i.e. a bolt having a concrete bond of about 20 cm. The amplitude scale and time scale coincide with FIG. 7. The excitation alternating voltage pulse comprised one period and had an amplitude of about 20 volts.

A distance axis has also been shown in FIG. 8, this axis being calculated from the propagation velocity of the longitudinal compression wave in a loose bolt and within the frequency band in question. It will be noticed, however, that the instantaneous propagation velocity in concrete-bonded portions is lower than the propagation velocity of 5.1 km/s determined experimentally in respect of a loose bolt. In the case of the illustrated bolts having bonding lengths of about 20 cm and 40 cm respectively the means propagation velocity fell by about 1% for each dm of bonding length.

In FIG. 8, the length of the bolt has been marked with a line on the distance axis beneath the excitation pulse reflected from the ends of respective bolts. In addition, a hatched area is shown on the distance axis, this hatched area corresponding to the position and length of the bond.

In FIG. 8, the reflected oscillation from the end of the bolt are shown approximately centrally in the figure. The reflected oscillations have considerably smaller amplitude than the corresponding oscillations reflected in the loose bolt shown in FIG. 7. On the other hand, the arrival time of the reflected signal from the end of the bolt in FIG. 8 coincides quite well with the arrival time shown in FIG. 7. Consequently, from the amplitude and arrival time of the reflected oscillations it is possible to draw the conclusion that the bolt is bonded along a part of its length. Immediately after the excitation pulse in FIG. 8, there are found reflected oscillations which indicate discontinuities along the bolt. In this case the discontinuities comprise the concrete bond.

With a bonding length of about 40 cm, corresponding to the bolt C in FIG. 6, there is obtained a signal configuration shown in FIG. 9. It will be seen from FIG. 9, that the reflected oscillation from the end of the bolt has a very small amplitude. The position of the concrete bond along the bolt and the length of said bond is shown by a hatched area in FIG. 9. The inner end of the bolt is marked with a line at the distance 225 cm. A reflected oscillation immediately after the excitation pulse indicates the discontinuity formed by the beginning of the concrete bond.

Figure 10:
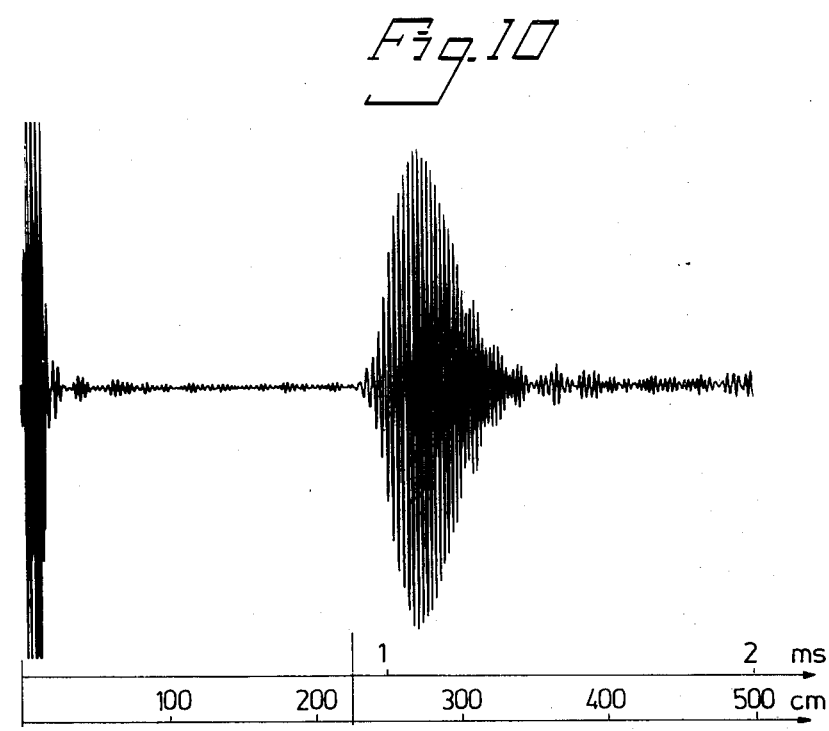
Figure 11:
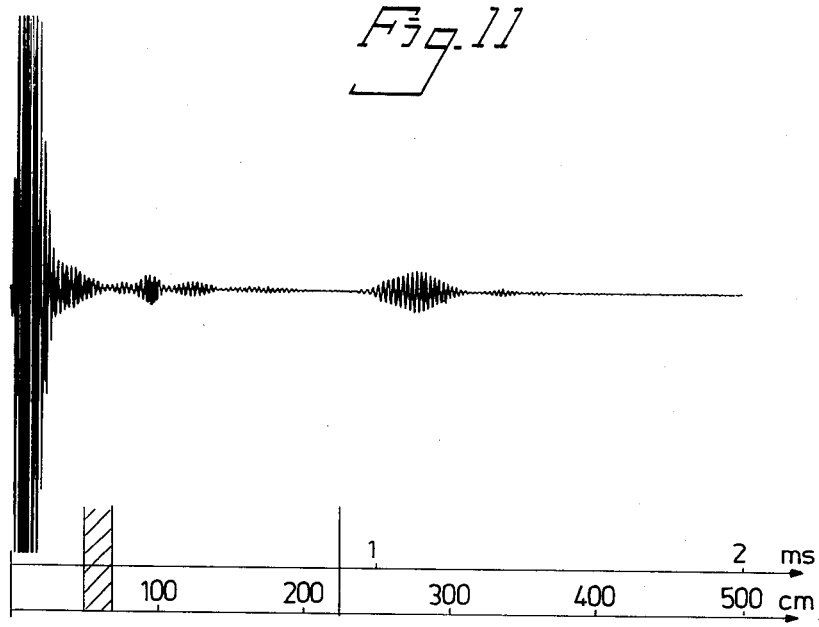
Figure 12:
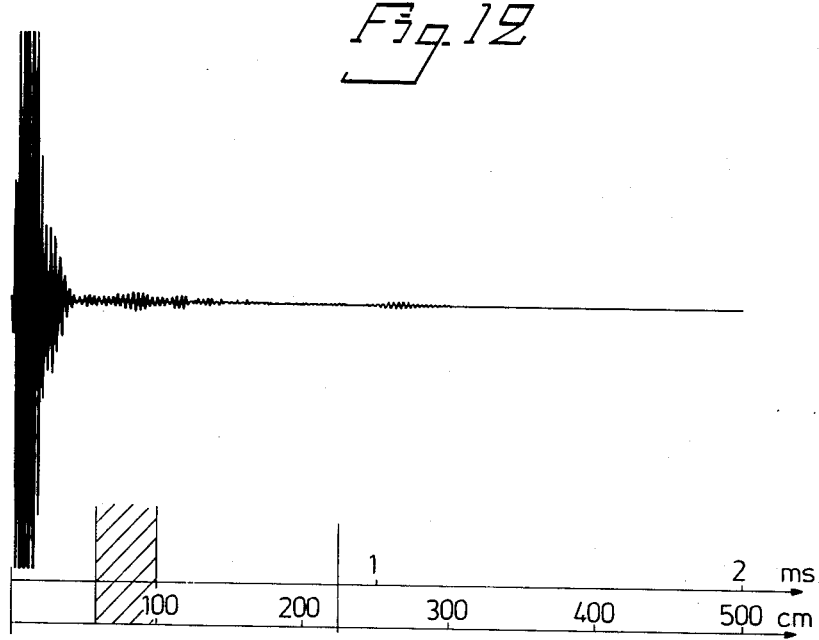

The signals shown in FIGS. 10-12 have been obtained with the same settings of the switching devices as those used when exciting and measuring the signals shown in FIGS. 7-9. The excitation wave type is thus substantially a longitudinal compression wave. The signals shown in FIGS. 10-12, however, have been obtained with a different filter setting, namely a pass band having a lower limit frequency of 60 kHz and an upper limit frequency of 100 kHz. FIGS. 10-12 are reproduced with the same amplitude scale and distance scale. The time scale in FIGS. 10-12 has also been supplemented with a distance scale and shows the position of the concrete bond along the bolt and the length of said bond. Excitation was effected with an alternating voltage pulse comprising one period of frequency 80 kHz.

FIG. 10 illustrates the signal configuration when measuring the loose bolt A shown in FIG. 6. Farthest to the left of the figure is shown the pulse of limited amplitude originating from the excitation signal. Approximately centrally of FIG. 10 there is shown the oscillation reflected from the inner end of the bolt. This oscillation in FIG. 10 is of much longer duration than the corresponding oscillation shown in FIG. 7. This may be caused by the excitation and detection device in FIG. 2 having resonances within the frequency range 60-100 kHz.

FIG. 11 illustrates the signal obtained when investigating the bolt B in FIG. 6 having a bond length of about 20 cm. Due to the fact that the bolt has been concrete-bonded to about 20 cm, the amplitude of the oscillation reflected from the inner end of the bolt has decreased, although the arrival time is substantially unchanged compared with the conditions in FIG. 10.

Finally, FIG. 12 shows the signal obtained when measuring a bolt having a concrete bond of about 40 cm, i.e. the bolt C shown in FIG. 6. The oscillation reflected from the free end of the bolt has been damped further, as a result of the longer concrete bond.

Figure 13:
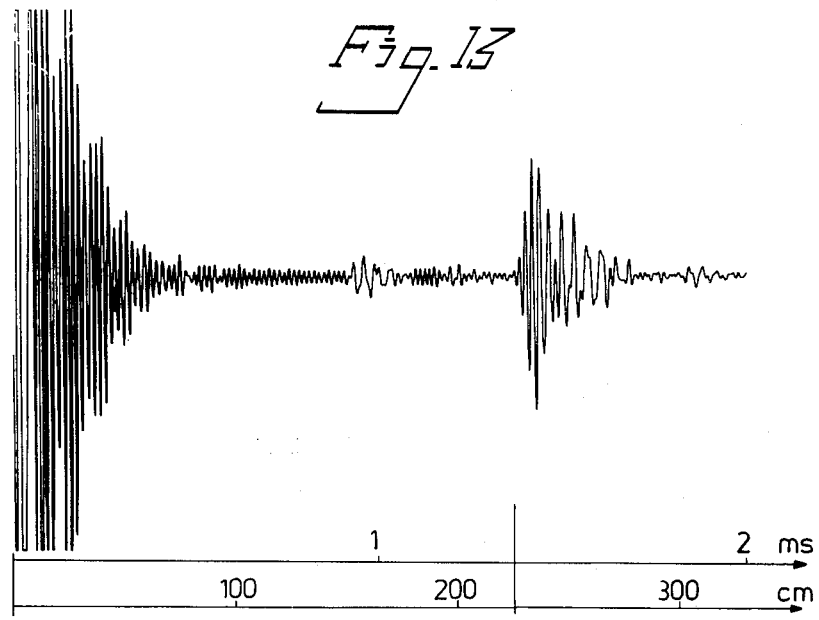
Figure 14:
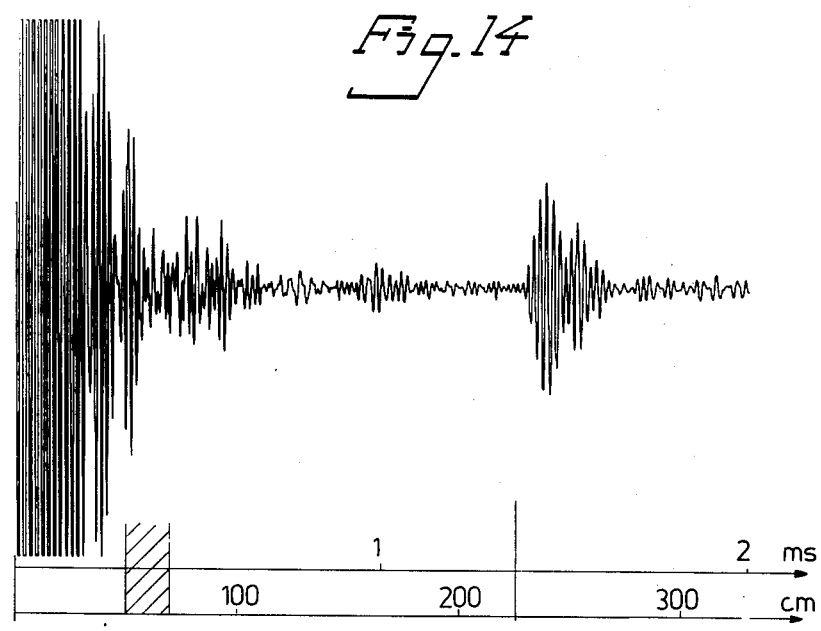
Figure 15:
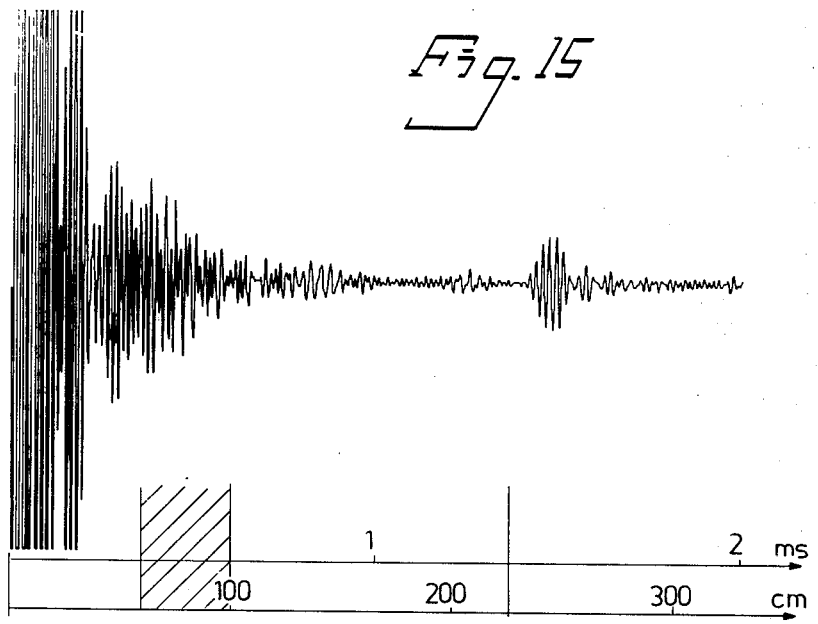

The signals shown in FIGS. 13-15 have been obtained with the switching device 21, FIG. 3, in a position such that there is applied to each of the two excitation electrodes an alternating voltage pulse of mutually the same amplitude but with 180° phase difference. In a corresponding manner, the switching device 24 was set so that the difference between the signals from the two detection electrode-halves was applied to the filter 26. These settings of the detection devices provide for excitation-and detection-sensivity in respect of flexural waves, whilst the longitudinal wave is suppressed. The lower limit frequency of the band-pass filter was here 40 kHz and the upper limit frequency 80 kHz. The frequency of the alternating voltage pulse was about 60 kHz and its amplitude about 20 volts. The FIGS. 13-15 have the same time scale as the FIGS. 7-12 but the distance scale differs considerably, due to the large difference in the propagation velocity of the longitudinal wave and flexural wave respectively. The propagation velocity for a flexural wave of this frequency in bolt A has been determined experimentally as being about 3.3 km/s. The propagation velocity in concrete-bonded parts of bolts of the type in question has been determined experimentally as being about 3 km/s.

The signal shown in FIG. 13 was obtained when investigating the loose bolt A shown in FIG. 6. The amplitude-limited pulse originating from the excitation is shown farthest to the left of the figure. In the case of a flexural wave, this pulse has a longer decay time than in the case of a lingitudinal wave. Shown to the right of FIG. 13 is the signal reflected from the end of the bolt. At the distance 160 cm, approximately centrally of FIG. 13, there is shown a reflected signal of the longitudinal wave mode, reflected from the inner end of the bolt. This has occurred as a result of irregularities in the testing equipment such as asymmetries in the excitation and detection device, eccentricity between the axes of the excitation and detection device and the bolt axis, and irregularities in the free end surface of the bolt.

FIG. 14 shows the signal when examining the bolt B shown in FIG. 6, which has been concrete-bonded to a length of about 20 cm. The characteristic of the excitation signal has been changed somewhat, due to the discontinuity created by the concrete bond. Compared with the conditions relating to the loose bolt in FIG. 13, the signal reflected from the inner end of the bolt has only been relatively slightly damped, due to the 20 cm long concrete bond. A smaller reflected signal is also found in FIG. 14 approximately at the distance 160 cm, due to the fact that it has not been possible to suppress the longitudinal wave completely.

FIG. 15 illustrates the signal obtained when investigating the bolt C shown in FIG. 6, which is concrete-bonded to about 40 cm, with flexural waves. The flexural wave reflected from the inner end of the bolt has a relatively large amplitude, despite the fact that the length of the bond is about 40 cm. Generally, the lowest oscillation mode of the flexural wave is damped much less per unit of length when propagating along a concrete-bonded bolt than the lowest oscillation mode of a longitudinal compression wave of the same frequency. By using flexural waves, it is therefore possible to examine bolts with much longer concrete bonds, than when solely longitudinal compression waves are used. On the other hand, under certain conditions the longitudinal compression wave of the lowest frequency is more suitable for determining the beginning of the concrete bond of a bolt having a free end projecting outwardly from the bond. By alternately exciting and detecting both wave types, it is therefore possible in certain cases to obtain better information about the bond than when merely using flexural waves. There are reasons to assume that the same also applies in the case of, for example, plastics-bonded bolts. In practice it can be problematic to observe the reflected signal from the beginning of the concrete bond, when the distance between the free end of the bolt and the beginning of the concrete bond is so short that signal reflections are obscured by the still decaying excitation signal. In order to be able to detect a reflection clearly from the beginning of the concrete bond, a distance means, for example, comprising a circular steel cylinder with flat end surfaces having the same diameter as the bolt, i.e. in this case a diameter of 25 mm, may be placed between the excitation and detection device and the free end of the bolt. The distance means 40 is shown only partially in FIG. 4 for reasons of space. Their actual length may be much longer than illustrated, i.e. 5 to 20 cm when the waves have frequencies between 20 and 100 kHz.

Figure 16:
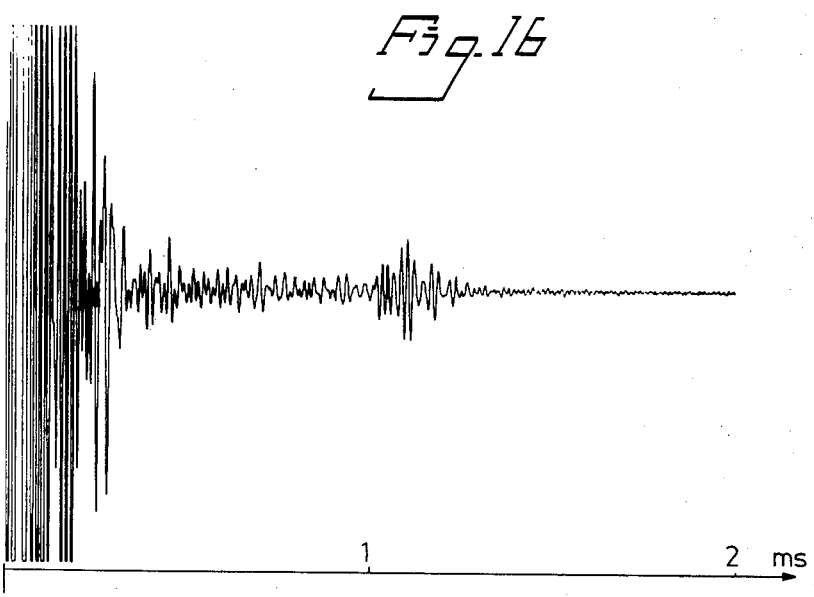
FIG. 16 illustrates the configuration of a signal obtained when investigating a shorter bolt.

For the purpose of illustrating the possibilities of the flexural wave, there is illustrated in FIG. 16 a signal configuration obtained when measuring a 150 cm long bolt bonded in concrete along 120 cms of its length. The signal reflected from the end of the bolt is shown clearly in the centre of the figure.

By way of summary it will be seen from the FIGS. 7–15 that the length of the bonded bolt can be roughly determined with knowledge of the propagation velocity of the type of wave when used and the time of arrival of the signal reflected from the inner end of the bolt. When measuring primarily with a longitudinal wave of low frequency it is possible by special observation of the signal from the time the excitation pulse has decayed to the time when the signal reflected from the inner end of the bolt has arrived, to determine if there is a discontinuity along the bolt and, if so, the position of said discontinuity therealong or at least the position of the beginning of a discontinuity. Damping of the waves per unit of length in free parts of a bolt and in parts whose concrete bond is satisfactory can be determined experimentally. Having knowledge of this damping and a rough idea of the length of the bolt, it is possible to obtain a rough idea of the length-quality of the bond with the aid of the total damping of waves reflected from the inner end of the bolt.

The examples given above and the described tests are only concerned with concrete-bonded bolts. There are reasons, however, to assume that by using the method or apparatus according to the invention it is also possible to determine the length of expander bolts, the position of the expanding part of the bolt and, at least to a certain extent, the extent of the contact between the expander and the surrounding material. Neither can the use of the method and apparatus according to the invention with other bonded rod-like bodies be excluded.

In case of a pretensioned bolt with either an expander or a bonding at the inner end there are reasons to assume that by using the method or apparatus according to the invention it is furthermore possible to determine approximately the extent of the contact between the bearing plate at the outer end of the bolt and the material underneath the plate. The extent of contact depends on the tension in the bolt. Thus it may be possible to estimate the tension in the bolt.

It is believed that the optimum frequency band is related to the diameter of the rod-like body. Accordingly it is believed that the optimum frequencies are higher when the diameter is smaller, and the optimum frequencies are lower when the diameter is larger.

Preferably should the wavelength of the flexural wave be a couple of times greater than the diameter of the rod.

We claim:

1. A method for investigating a rod-like body which is anchored in a surrounding material and which has an accessible end, for selectively determining the state of the anchorage of said body and its anchored length by the excitation of transient elastic oscillations in said accessible end of said body and by the detection at said accessible end of transient elastic oscillations reflected at ends or other discontinuities of said body and/or said anchorage, said method comprising
exciting at least at certain times in said end oscillations of a predetermined flexural wave mode type which has a neutral plane located substantially parallel with the longitudinal axis of said body, said predetermined flexural wave mode type causing certain parts of a cross section of said body on one side of said neutral plane to be expanded in the longitudinal direction of said body while at the same time causing other corresponding parts of said cross section of said body on the opposite side of said neutral plane to be compressed in said longitudinal direction of said body,
separating and identifying oscillations of said predetermined flexural wave mode type among received reflected oscillations at least at times corresponding to said certain times by a manner of receiving oscillations sensitive to oscillations of said predetermined flexural wave mode type while simultaneously suppressing the influence of oscillations of a predetermined longitudinal wave mode type, said predetermined longitudinal wave mode type causing successive compression and expansion in said longitudinal direction of said body of substantially whole cross sections of said body,
estimating the position and/or type and/or magnitude of said discontinuities with the aid of the time position and amplitude of said detected reflected transient elastic oscillations of said predetermined flexural wave mode type, and
selectively determining one or both of said state of said anchorage and said anchored length of said body with the aid of said estimated discontinuities.

2. A method according to claim 1, comprising
exciting simultaneously with or at times other than said certain times oscillation of a predetermined longitudinal wave mode type, said predetermined longitudinal wave mode causing successive compression and expansion in the longitudinal direction of said body of substantially whole cross sections of said body,
separating and identifying oscillations of said predetermined longitudinal wave mode type among received reflected oscillations simultaneously with or at times corresponding to said times other than said certain times by a manner of receiving oscillations sensitive to oscillations of said predetermined longitudinal wave mode type while simultaneously suppressing the influence of oscillations of said predetermined flexural wave mode type, and
using also the time position and amplitude of said detected reflected transient elastic oscillations of said predetermined longitudinal wave mode type for the estimation of the position and/or magnitude and/or type of said discontinuities.

3. A method according to claim 1 or 2 for investigating a concrete-bonded bolt wherein the detection reflected oscillations lie in the frequency range of about 20–100 kHz.

4. A method for investigating a rod-like body which is anchored in a surrounding material and which has an accessible end, for selectively determining the state of the anchorage of said body and its anchored length by the excitation of transient elastic oscillations in said accessible end of said body and by the detection at said accessible end of transient elastic oscillations reflected at ends or other discontinuities of said body and/or said anchorage, said method comprising,
applying at least at certain times to different areas of said accessible end excitation in the form of transient oscillatory deformations with phase and amplitude relationships selected so as to promote the generation of oscillations of a predetermined flexural wave mode in said accessible end thereby to cause said excited transient elastic oscillations to include oscillations of said predetermined flexural wave mode type, sensing at different areas of said accessible end deformations in said accessible end caused by said reflected transient elastic oscillations, creating deformation signals corresponding respectively to said deformations sensed at said different areas, combining said deformation signals into output signals indicating time position and amplitude of said sensed reflected transient oscillations, said combining at times corresponding to said certain times being done in a predetermined way enhancing the effect upon at least one of said output signals caused by sensed reflected transient elastic oscillations of said predetermined flexural wave mode type while suppressing the influence upon said at least one output signal caused by sensed reflected transient elastic oscillations of a predetermined longitudinal wave mode type, said predetermined longitudinal wave mode causing successive compression and expansion in the longitudinal direction of said body of substantially whole cross sections of said body, estimating the position and/or magnitude and/or type of said discontinuities with the aid of time position and amplitude of said detected reflected transient elastic oscillations indicated by said output signals, and selectively determining one or both of said state of said anchorage and said anchored length of said body with the aid of said estimated discontinuities.

5. A method according to claim 4 for investigating a concrete-bonded bolt wherein the detected reflected oscillations lie in the frequency range about 20–100 kHz.

6. A method according to claim 1 or 4, wherein the excitation comprises not more than a few periods of oscillation at a time.

7. An apparatus for investigating a rod-like body which is anchored in a surrounding material and which has an accessible end, for selectively determining the state of the anchorage of said body and its anchored length by the excitation of transient elastic oscillations in said accessible end of transient elastic oscillations reflected at ends of other discontinuities of said body and/or said anchorage, said apparatus comprising, excitation means for exciting at least at certain times in said end oscillations of a predetermined flexural wave mode type which has a neutral plane located substantially parallel with the longitudinal axis of said body, said predetermined flexural wave mode type causing certain parts of a cross-section of said body on one side of said neutral plane to be expanded in the longitudinal direction of said body while at the same time causing other corresponding parts of said cross section of said body on the opposite side of said neutral plane to be compressed in said longitudinal direction of said body, detection means including flexural mode detection means and flexural mode separating means for at times corresponding to said certain times making said flexural mode detection means sensitive to oscillations of said predetermined flexural wave mode type while simultaneously suppressing the influence of oscillations of a predetermined longitudinal wave mode type, said predetermined longitudinal wave mode causing successive compression and expansion in said longitudinal direction of said body of substantially whole cross sections of said body, means for estimating the position and/or type and/or magnitude of said discontinuities with the aid of time-position and amplitude of said detected reflected transient elastic oscillations of said predetermined flexural wave mode type, and means for selectively determining one or both of said state of said anchorage and said anchored length of said body with the aid of said estimated discontinuities.

8. An apparatus according to claim 7 wherein said excitation means includes means for exciting simultaneously with or at times other than said certain times oscillations in said accessible end of said predetermined longitudinal wave type, and said detection means includes longitudinal wave mode detection means and longitudinal wave mode separating means for at times simultaneously with said certain times or at times corresponding to said times other than said certain times making said longitudinal mode detection means sensitive to oscillations of said predetermined longitudinal wave mode type while simultaneously suppressing the influence of oscillations of said predetermined flexural wave mode type.

9. An apparatus for investigating a rod-like body which is anchored in a surrounding material and which has an accessible end for selectively determining the state of the anchorage of said body and the length thereof, by the excitation and detection of transient elastic oscillations in said accessible end, said apparatus comprising, excitation means for applying at certain times to different areas of said accessible end in the form of transient oscillatory deformations with predetermined phase and amplitude relationships promoting the generation of oscillations of a predetermined flexural wave mode type in said accessible end while at the same time suppressing the generation of oscillations of a predetermined longitudinal wave mode type in said accessible end thereby to cause said excitated transient elastic oscillations to be mainly of said predetermined flexural wave mode type at said certain times, sensing and deformation signals generating means for sensing at different areas of said accessible end deformations in said accessible end caused by transient elastic oscillations reflected at ends or other discontinuities of said body and/or said anchorage and for generating deformation signals corresponding to said deformations sensed at said different areas, signals combining and output signals generating means responsive to said deformation signals for generation of output signals indicating the time-position and amplitude of said sensed reflected transient elastic oscillations, said signals combining and output signals generating means including mode selecting means for at times corresponding to said certain times combine said deformation signals into at least one output signal in a predetermined way enhancing the effect upon said output signal caused by sensed reflected transient elastic oscillations of said predetermined flexural wave mode type while simultaneously suppressing the effect upon said output signal caused by sensed reflected transient elastic oscillations of said predetermined longitudinal wave mode type, and estimation and determining means for estimation of the position and/or type and/or magnitude of said discontinuities with the aid of the time-position and amplitude of said sensed reflected transient elastic oscillations indicated by said output signals and for selectively determining one or both of said state of anchorage and said length of said body with the aid of said estimated discontinuities.

10. An apparatus according to claim 9 wherein said excitation means and said sensing and deformation signals generating means each or in common includes two cylindrical electro-mechanical converters, said excitation means includes two excitation electrodes having mutually adjacent substantially identical surfaces which together have a size and shape which substantially corresponds to the cross-sectional area of one of said converters, and said sensing and deformation signals generating means includes two detection electrodes having mutually adjacent substantially identical surfaces which together have a size and shape which substantially corresponds to the cross-sectional area of one of said converters.

11. An apparatus according to claim 9 wherein said excitation means and said sensing and deformation signals generating means each or in common includes two cylindrical electro-mechanical converters, said excitation means includes two excitation electrodes having mutually adjacent substantially identical surfaces which together have a size and shape which substantially corresponds to the cross-sectional area of one of said converters, said sensing and deformation signals generating means includes four detection electrodes having mutually adjacent substantially identical surfaces which together have a size and a shape which substantially corresponds to the cross-sectional area of one of said converters.

12. An apparatus for investigating an anchored rod-like body which is anchored in a surrounding material and which has an accessible end, by the excitation of transient elastic oscillations in said accessible end of said body and by the detection of said accessible end of transient elastic oscillations reflected at the ends of or any other discontinuities of said body and/or said anchorage, said apparatus comprising, means for applying at certain times excitation mainly of a predetermined flexural wave mode type which has a neutral plane located substantially parallel with the longitudinal axis of said body, and predetermined flexural wave mode type causing certain parts of a cross-section of said body on one side of said neutral plane to be expanded in the longitudinal direction of said body while at the same time causing other corresponding parts of said cross section of said body on the opposite side of said neutral plane to be compressed in said longitudinal direction of said body, detection means including mode separation means for at times corresponding to said certain times making said detection of reflected transient elastic oscillations sensitive to oscillations of said predetermined flexural wave mode type while simultaneously suppressing the influence of oscillations of a longitudinal wave mode type at said detection, means for determining the time-position and amplitude of detected transient elastic oscillations of said predetermined flexural wave mode type reflected at any of said discontinuities or ends of said body and/or anchorage, and means to ascertain the distance of reflections of elastic oscillations caused at any points of discontinuity or at the end of the length of said rod-like body.

13. An apparatus for investigating an anchored rod-like body which is anchored in a surrounding material and has an accessible end by the excitation of transient elastic oscillations in said accessible end and by the detection at said accessible end of transient elastic oscillations reflected at discontinuities of said body and or said anchorage, means for the excitation and detection of both or a selected one of a predetermined flexural wave mode and a predetermined longitudinal wave mode, said means comprising, at least four circular-cylindrical electro-mechanical converters arranged in a manner such that their axes substantially coincide, at least three circular electrically conductive electrodes, two semi-circular excitation electrodes arranged side by side between a first and a second of the converters, two semi-circular detection electrodes arranged side by side between a third and a fourth of the converters, a first of the circular electrodes being arranged adjacent the first converter on the side thereof opposite to the excitation electrodes, another of the circular electrodes being arranged between the second and the third converter, the third circular electrode being arranged adjacent the fourth converter on the side thereof opposite to the detection electrodes, and the electrodes and the converters being bonded together to form a substantially circular-cylindrical body, and more selective electronic circuitry for applying at excitation alternating electric signals with selective predetermined phase and amplitude relationships to the two semi-circular excitation electrodes and for receiving at detection alternating electric signals from the two semi-circular detection electrodes and combining the last mentioned signals with selective predetermined phase and amplitude relationships.

14. In an apparatus for investigating an anchored rod-like body which is anchored in a surrounding material and has an accessible end by the excitation of transient elastic oscillations in said accessible end and by the detection at said accessible end of transient elastic oscillations reflected at end of or other discontinuities of said body and/or said anchorage, means for the excitation and detection of both or a selected one of a predetermined longitudinal wave mode and a predetermined flexural wave mode having a neutral plane in any one or both of two mutually perpendicular planes parallel to the longitudinal direction of said body, said means comprising, at least four circular cylindrical electro-mechanical converters arranged in a manner such that their axes substantially coincide, at least three circular electrically conductive electrodes, two semi-circular excitation electrodes arranged side by side in between a first and a second of the converters, and four quarter-circular detection electrodes arranged side by side between a third and a fourth of the converters, a first of the circular electrodes being arranged adjacent the first converter on the opposite side to the excitation electrodes, a further of the circular electrodes being arranged between the second and the third converter, the third circular electrode being arranged adjacent the fourth converter on the opposite side to the fourth detection electrode and the converters being bonded together to form a substantially circular-cylindrical body, and wave mode selecting electronic circuitry for applying at excitation alternating electric signals with selective predetermined phase and amplitude relationships to the two semi-circular excitation electrodes and for receiving at detection alternating electric signals from the four quarter-circular detection electrodes and combining the last mentioned signals with selective predetermined phase and amplitude relationships.

15. A method for investigating a rod-like body which is anchored in a surrounding material and which has an accessible end, by the excitation of transient elastic oscillations in said accessible end of said body and by the detection at said accessible end of transient elastic oscillations reflected at discontinuities of said anchorage and/or in the length of the body and/or from the end of said body or anchorage, said method comprising, applying at certain times excitation mainly of a predetermined flexural wave mode type which has a neutral plane located substantially parallel with the longitudinal axis of said body, said predetermined flexural wave mode type causing certain parts of a cross section of said body on one side of said neutral plane to be expanded in the longitudinal direction of said body while at the same time causing other corresponding parts of said cross section of said body on the opposite side of said neutral plane to be compressed in said longitudinal direction of said body, at times corresponding to said certain times making said detection of reflected transient elastic oscillations sensitive to oscillations of said predetermined flexural wave mode type while simultaneously suppressing the influence of oscillations of a longitudinal wave mode at said detection, determining time-position and amplitude of detected transient elastic oscillations of the predetermined flexural wave mode reflected from any of said discontinuities or said ends, estimating selectively any of the position, type and magnitude of said discontinuities and ends with the aid of said time-position and amplitude of said detected reflected oscillations, and determining the distance of any said discontinuity or said end of said anchorage or body with the aid of said estimated quantities including position, type and magnitude.

16. A method for investigating a rod-like body which is anchored in a surrounding material and which has an accessible end, for selectively determining the state of the anchorage of said body and its anchored length by the excitation of transient elastic oscillations in said accessible end of said body and by the detection at said accessible end of transient elastic oscillations reflected at ends or other discontinuities of said body and/or said anchorage, said method comprising, applying at certain times excitation mainly of a predetermined flexural wave mode type which has a neutral plane located substantially parallel with the longitudinal axis of said body, said predetermined flexural wave mode type causing certain parts of a cross section of said body on one side of said neutral plane to be expanded in the longitudinal direction of said body while at the time causing other corresponding parts of said cross section of said body on the opposite side of said neutral plane to be compressed in said longitudinal direction of said body, at times corresponding to said certain times making said detection of reflected transient elastic oscillations sensitive to oscillations of said predetermined flexural wave mode type while simultaneously suppressing the influence of oscillations of a longitudinal wave mode at said detection, estimating the position and/or type and/or magnitude of said discontinuities with the aid of the time position and amplitude of said detected reflected transient elastic oscillations, and selectively determining one or both of said state of said anchorage and the length of said body with the aid of said estimated discontinuities.

17. A method according to claim 16, comprising, applying at times other than said certain times excitation mainly of a predetermined longitudinal wave mode type, said predetermined longitudinal wave mode causing successive compression and expansion in the longitudinal direction of said body of substantially whole cross sections of said body, and at times corresponding to said times other than said certain times making said detection of reflected transient elastic oscillations sensitive to oscillations of said predetermined longitudinal wave mode type while simultaneously suppressing the influence of oscillations of said predetermined flexural wave mode type at said detection.

18. A method for investigating a rod-like body which is anchored in a surrounding material and which has an accessible end, for selectively determining the state of the anchorage of said body and its anchored length by the excitation of transient elastic oscillations in said accessible end of said body and by the detection at said accessible end of transient elastic oscillations reflected at discontinuities of said body and/or said anchorage, said method comprising, applying at certain times to different areas of said accessible end excitation in the form of transient oscillatory deformations with phase and amplitude relationships selected so as to promote the generation of oscillations of a predetermined flexural wave mode in said accessible end while at the same time suppressing the generation of oscillations of a predetermined longitudinal wave mode in said accessible end, thereby to cause said excited transient elastic oscillations to be mainly flexural waves of said predetermined wave mode type, at said detection sensing at different areas of said accessible end deformations in said accessible end caused by said reflected transient elastic oscillations, at said detection creating deformation signals corresponding respectively to said deformations sensed at said different areas, combining said deformation signals into output signals indicating time-position and amplitude of said sensed reflected transient oscillations, said combining at times corresponding to said certain times being done in a predetermined way enhancing the effect upon said output signals caused by sensed reflected transient elastic oscillations of said predetermined flexural wave mode type while at the same time suppressing the influence upon said output signals caused by sensed reflected transient elastic oscillations of said predetermined longitudinal wave mode type, estimating the position and/or magnitude and/or type of said discontinuities with the aid of the time-position and amplitude of said detected reflected transient elastic oscillations indicated by said output signals, and selectively determining one or both of said state of said anchorage and said anchored length of said body with the aid of said estimated discontinuities.

* * * * *